United States Patent
Kashima et al.

(10) Patent No.: US 9,982,087 B2
(45) Date of Patent: May 29, 2018

(54) METHOD FOR PRODUCING COMPOUND

(71) Applicant: Sumitomo Chemical Company, Limited, Tokyo (JP)

(72) Inventors: Ken Kashima, Osaka (JP); Noriyuki Hida, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days. days.

(21) Appl. No.: 14/912,946

(22) PCT Filed: Jul. 31, 2014

(86) PCT No.: PCT/JP2014/070797
§ 371 (c)(1),
(2) Date: Feb. 19, 2016

(87) PCT Pub. No.: WO2015/025719
PCT Pub. Date: Feb. 26, 2015

(65) Prior Publication Data
US 2016/0200861 A1    Jul. 14, 2016

(30) Foreign Application Priority Data

Aug. 22, 2013   (JP) ................................ 2013-171999

(51) Int. Cl.
| | |
|---|---|
| *C07C 69/76* | (2006.01) |
| *C08G 61/12* | (2006.01) |
| *C07C 67/465* | (2006.01) |
| *C07C 209/60* | (2006.01) |
| *C07C 1/32* | (2006.01) |

(52) U.S. Cl.
CPC ............ *C08G 61/121* (2013.01); *C07C 1/321* (2013.01); *C07C 67/465* (2013.01); *C07C 209/60* (2013.01); *C08G 61/12* (2013.01); *C08G 61/122* (2013.01); *C07C 2531/22* (2013.01); *C07C 2531/24* (2013.01); *C07C 2603/18* (2017.05); *C08G 2261/1424* (2013.01); *C08G 2261/1426* (2013.01); *C08G 2261/3142* (2013.01); *C08G 2261/3162* (2013.01); *C08G 2261/3245* (2013.01); *C08G 2261/411* (2013.01)

(58) Field of Classification Search
CPC ..... C07C 1/321; C07C 13/567; C07C 209/60; C07C 2103/18; C07C 2531/22; C07C 2531/24; C07C 67/465; C07C 2603/18; C08G 2261/1424; C08G 2261/1426; C08G 2261/3142; C08G 2261/3162; C08G 2261/3245; C08G 2261/411; C08G 61/12; C08G 61/121; C08G 61/122
See application file for complete search history.

(56) References Cited

U.S. PATENT DOCUMENTS

| | | | |
|---|---|---|---|
| 5,777,070 A | 7/1998 | Inbasekaran et al. | |
| 2011/0187266 A1* | 8/2011 | Fukushima | C08G 61/02 313/504 |

FOREIGN PATENT DOCUMENTS

| | | |
|---|---|---|
| JP | 2001520289 A | 10/2001 |
| JP | 3310658 B1 | 8/2002 |
| JP | 2008056911 A | 3/2008 |
| JP | 2012072310 A | 4/2012 |
| JP | 2013229429 A | 11/2013 |
| WO | 0053656 A1 | 9/2000 |

OTHER PUBLICATIONS

Fu et al. (Parameters Influencing the Molecular Weight of 3,6-Carbazole-Based D-p-A-Type Copolymers, Journal of Polymer Science Part A: Polymer Chemistry 2011, 49, 4368-4378, as cited in the IDS filed Feb. 19, 2016).*
International Search Report (with English translation) and Written Opinion dated Oct. 14, 2014 in International Application No. PCT/JP2014/070797.
Sonntag et al., "Novel 2,7-Linked Carbazole Trimers as Model Compounds for Conjugated Carbazole Polymers," Chemistry of Materials, vol. 16, pp. 4736-4742 (2004).
Fu et al., "Parameters Influencing the Molecular Weight of 3,6-Carbazole-Based D-p-A-Type Copolymers," Journal of Polymer Science Part A: Polymer Chemistry, vol. 49, pp. 4368-4378 (2011).
Kim et al., "Carbazole-Based Copolymers: Effects of Conjugation Breaks and Steric Hindrance," Macromolecules, vol. 44, pp. 1909-1919 (2011).
Calò et al., "Pd Nanoparticles as Efficient Catalysts for Suzuki and Stille Coupling Reactions of Aryl Halides in Ionic Liquids," Journal of Organic Chemistry, vol. 70, pp. 6040-6044 (2005).
Lin et al., "Enhancing Activity of Suzuki Reactions in Water by Using Guanidinium Ionic Liquid Stabilized Palladium Micelle Catalyst," Synlett, vol. 12, pp. 1779-1783 (2011).
Extended Search Report dated Mar. 1, 2017 in EP Application No. 14838250.0.
Suzuki, Akira, "TCI Male," Tokyo Chemical Industry Co. Ltd., vol. 4, No. 142, pp. 2-23 (2009).

(Continued)

*Primary Examiner* — Yevgeny Valenrod
*Assistant Examiner* — Blaine G Doletski
(74) *Attorney, Agent, or Firm* — Panitch Schwarze Belisario & Nadel LLP

(57) ABSTRACT

A method is provided for producing a compound, including a step of mixing a compound (1) having one or two leaving groups, a compound (2) having one or two boron atom-containing leaving groups, an organic base (P), and at least one selected from a phase transfer catalyst and an organic base (Q) larger in the number of carbon atoms than the above-mentioned organic base in the presence of a transition metal catalyst. The method thereby performs a coupling reaction between the above-mentioned compound (1) and the above-mentioned compound (2).

12 Claims, No Drawings

(56) References Cited

OTHER PUBLICATIONS

Office Action dated Feb. 21, 2018 in JP Application No. 2015-532800.

* cited by examiner

METHOD FOR PRODUCING COMPOUND

CROSS-REFERENCE TO RELATED APPLICATION

This application is a Section 371 of International Application No. PCT/JP2014/070797, filed Jul. 31, 2014, which was published in the Japanese language on Feb. 26, 2015, under International Publication No. WO 2015/025719 A1, and the disclosure of which is incorporated herein by reference.

TECHNICAL FIELD

The present invention relates to a method for producing a compound.

BACKGROUND ART

A coupling reaction between condensing an organohalogen compound and a boron compound under a basic condition is known as a method for producing a compound which gives high versatility. Compounds obtained by conducting the coupling reaction are utilized in medical drugs, agricultural chemicals, liquid crystal materials, organic electronics materials and the like.

However, the above-described coupling reaction shows an insufficient reaction rate in some cases.

As the method for raising the reaction rate of the above-described coupling reaction, there are reports on a method for adding a phase transfer catalyst to an inorganic base (patent document 1, non-patent document 1) and a method for using an organic base (patent document 2).

PRIOR ART DOCUMENT

Patent Document

Patent document 1: Japanese Patent Application National Publication No. 2001-520289
Patent document 2: Japanese Patent No. 3310658

Non-Patent Document

Non-patent document 1: Chem. Mater. 2004, 16, 4736-4742

SUMMARY OF THE INVENTION

Problem to be Solved by the Invention

A method for producing a compound showing a further higher reaction rate has been desired.

Means for Solving the Problem

The present invention includes the following inventions.

[1] A method for producing a compound, comprising mixing a compound (1) having one or two leaving groups, a compound (2) having one or two boron atom-containing leaving groups, an organic base (P), and at least one selected from the group consisting of a phase transfer catalyst and an organic base (Q) larger in the number of carbon atoms than the above-mentioned organic base in the presence of a transition metal catalyst, thereby performing a coupling reaction between the above-mentioned compound (1) and the above-mentioned compound (2).

[2] The method for producing a compound according to [1], wherein the leaving group which the compound (1) has is a halogen atom, a diazonio group or a group represented by $-O-S(=O)_2R^{C1}$, wherein $R^{C1}$ represents an alkyl group or an aryl group and these groups optionally have a substituent.

[3] The method for producing a compound according to [1] or [2], wherein the phase transfer catalyst is an ammonium compound.

[4] The method for producing a compound according to any one of [1] to [3], wherein the phase transfer catalyst is an ammonium compound having 16 to 60 carbon atoms.

[5] The method for producing a compound according to any one of [1] to [4], wherein the phase transfer catalyst is at least one selected from the group consisting of $(C_4H_9)_4NF$, $(C_4H_9)_4NCl$, $(C_4H_9)_4NBr$, $(C_4H_9)_4NI$, $(C_5H_{11})_4NCl$, $(C_5H_{11})_4NBr$, $(C_5H_{11})_4NI$, $(C_{16}H_{33})(CH_3)_3NCl$, $(C_8H_{17})_3(CH_3)NCl$, $(C_8H_{17})_2(C_{10}H_{21})(CH_3)NCl$, $(C_8H_{17})(C_{10}H_{21})_2(CH_3)NCl$, $(C_{10}H_{21})_3(CH_3)NCl$ and $(C_8H_{17})_4NBr$.

[6] The method for producing a compound according to any one of [1] to [5], wherein the organic base (P) is an organic base having 4 to 15 carbon atoms.

[7] The method for producing a compound according to any one of [1] to [6], wherein the organic base (P) is an ammonium hydroxide compound having 4 to 15 carbon atoms.

[8] The method for producing a compound according to any one of [1] to [7], wherein the organic base (Q) is an organic base having 16 to 60 carbon atoms.

[9] The method for producing a compound according to any one of [1] to [8], wherein the organic base (Q) is an ammonium hydroxide compound having 16 to 60 carbon atoms.

[10] The method for producing a compound according to any one of [1] to [9], wherein the transition metal catalyst is a palladium catalyst.

[11] The method for producing a compound according to any one of [1] to [10], wherein the compound (1) is a compound represented by the formula (A) and the compound (2) is a compound represented by the formula (B):

[wherein,
$R^1$ and $R^2$ each independently represent an organic group.
$X^1$ represents Cl, Br, I or $-O-S(=O)_2R^{C1}$, wherein $R^{C1}$ represents an alkyl group or an aryl group and these groups optionally have a substituent.
$X^2$ represents $B(R^{C2})_2$, $B(OR^{C2})_2$ or $BF_3T$, wherein $R^{C2}$ represents a hydrogen atom, an alkyl group or an aryl group and these groups optionally have a substituent, and the $R^{C2}$s may be the same or different and they may be combined together to form a ring (namely, a cyclic structure) together with the boron atom to which they are attached or together with the oxygen atoms to which they are attached and the boron atom to which the oxygen atoms are attached, and T represents Li, Na, K, Rb or Cs.
n and m each independently represent 1 or 2.].

[12] The method for producing a compound according to [11], wherein n and m are 1.

[13] The method for producing a compound according to [11], wherein n and m are 2.

[14] The method for producing a compound according to any one of [11] to [13], wherein $R^1$ and $R^2$ each independently represent an organic group having 1 to 60 carbon atoms.

[15] The method for producing a compound according to [14], wherein the organic group is an aromatic group having 6 to 20 carbon atoms and optionally having a substituent.

Effect of the Invention

According to the present invention, a method for producing a compound showing a high reaction rate can be provided.

MODES FOR CARRYING OUT THE INVENTION

The present invention will be illustrated in detail below.
<Compound (1) Having One or Two Leaving Groups>

The compound (1) having one or two leaving groups (hereinafter, referred to as a compound (1) in some cases) is usually an organic compound having a molecular weight of $1 \times 10^4$ or lower and having one or two leaving groups, and it is a compound dissolvable in an organic solvent.

The leaving group of the compound (1) is a group which leaves by reacting with the compound (2) having one or two boron atom-containing leaving groups, in the coupling reaction in the present invention.

The leaving group includes halogen atoms such as a chlorine atom, a bromine atom and an iodine atom; a diazonio group, a group represented by $-O-S(=O)_2R^{C1}$ (wherein, $R^{C1}$ represents an alkyl group or an aryl group and these groups optionally have a substituent) and the like. The diazonio group usually forms a salt with $HSO_4^-$, $Cl^-$, $Br^-$, $NO_3^-$, $ClO_4^-$, $BF_4^-$, $PF_6^-$ or the like. The group represented by $-O-S(=O)_2R^{C1}$ includes a mesylate group, a trifluoromethanesulfonate group, a p-toluenesulfonate group and the like. The leaving group includes preferably a chlorine atom, a bromine atom, a mesylate group and a trifluoromethanesulfonate group, more preferably a chlorine atom and a bromine atom, further preferably a bromine atom.

The compound (1) is preferably a compound represented by the formula (A) (hereinafter, referred to as a compound (A) in some cases):

$$R^1-(X^1)_n \quad (A)$$

[wherein, $R^1$ represents an organic group. $X^1$ represents Cl, Br, I or $-O-S(=O)_2R^{C1}$, wherein $R^{C1}$ represents an alkyl group or an aryl group and these groups optionally have a substituent. n represents 1 or 2.].

$R^1$ is preferably an organic group having 1 to 60 carbon atoms, more preferably an organic group having 6 to 20 carbon atoms. The organic group includes an aromatic group which optionally have a substituent, an organometal group which optionally have a substituent and an aliphatic hydrocarbon group which optionally have a substituent, preferably an aromatic group which optionally have a substituent and an organometal group which optionally have a substituent, more preferably an aromatic group having 6 to 20 carbon atoms which optionally have a substituent.

The above-mentioned aromatic group is an aromatic hydrocarbon group or an aromatic heterocyclic group. The above-mentioned aromatic hydrocarbon group is an aryl group or an arylene group. The above-mentioned aromatic heterocyclic group is a heteroaryl group or a heteroarylene group.

The number of carbon atoms of the aryl group is usually 6 to 60, preferably 6 to 20, more preferably 6 to 13.

The aryl group includes a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group and a 4-phenylphenyl group. A hydrogen atom in these groups are optionally substituted with an alkyl group, an alkenyl group, an alkynyl group, an alkoxy group, an aryloxy group, an aryl group, a heteroaryl group, an amino group, a substituted amino group, a fluorine atom, a group represented by the following formula (E-1):

$$-(X)_p-COOR' \quad (E-1)$$

[wherein, X represents an alkylene group or an oxyalkylene group. R' represents a hydrogen atom, an alkyl group or an aryl group. p represents an integer of 0 to 4. When there are a plurality of X, they may be the same or different.], a group represented by the following formula (E-2):

$$\text{(E-2)}$$

[wherein, R' represents the same meaning as described above. q represents an integer of 1 to 5. When there are a plurality of R', they may be the same or different.], a group represented by the following formula (E-3):

$$-(Y)_r-N^+(R'')_3Z^- \quad (E-3)$$

[wherein, Y represents an alkylene group or an oxyalkylene group. R'' represents a hydrogen atom, an alkyl group or an aryl group. $Z^-$ represents $F^-$, $Cl^-$, $Br^-$, $I^-$, $(C_6H_5)_4B^-$, $CH_3CO^-$ or $CF_3SO_3^-$. r represents an integer of 0 to 4. When there are a plurality of Y, they may be the same or different. The R''s may be the same or different.], and the like.

The explanations of the aryl group described above are equally applicable in the present specification.

The alkylene group represented by X or Y usually has 1 to 8 carbon atoms, and examples thereof include a methylene group, an ethylene group, a propylene group, a butylene group, an octylene group and the like.

The oxyalkylene group represented by X or Y is a group obtained by linking the above-described alkylene group with an oxygen atom.

The group represented by the formula (E-1) includes, for example, groups represented by the following formulae.

$-COOR' -(CH_2)_8-COOR' -O-(CH_2)_8-COOR' (OCH_2CH_2)_4-COOR'$

[wherein, the group represented by R' represents the same meaning as described above.].

The group represented by the formula (E-2) includes, for example, groups represented by the following formulae.

[wherein, the group represented by R' represents the same meaning as described above.].

The group represented by the formula (E-3) includes, for example, groups represented by the following formulae.

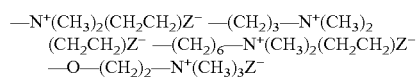

—N⁺(CH₃)₂(CH₂CH₂)Z⁻   —(CH₂)₃—N⁺(CH₃)₂(CH₂CH₂)Z⁻   —(CH₂)₆—N⁺(CH₃)₂(CH₂CH₂)Z⁻
—O—(CH₂)₂—N⁺(CH₃)₃Z⁻

[wherein, $Z^-$ represents the same meaning as described above.]

The alkoxy group is a group obtained by linking an alkyl group with an oxygen atom, and the alkyl group is as described later, and these are equally applicable in the present specification.

The aryloxy group is a group obtained by linking an aryl group with an oxygen atom, and it is equally applicable in the present specification.

The number of carbon atoms of the alkenyl group and the alkynyl group is usually 2 to 8.

The substituted amino group is a group obtained by partially or totally substituting hydrogen atoms of an amino group with a substituent, and the number of carbon atoms thereof, including the number of carbon atoms of a substituent, is usually 1 to 20. The substituted amino group includes a diphenylamino group and the like.

The number of carbon atoms of the arylene group, not including the number of carbon atoms of a substituent, is usually 6 to 60, preferably 6 to 30, more preferably 6 to 18.

The arylene group includes a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group and a chrysenediyl group. A hydrogen atom of these groups are optionally substituted with an alkyl group, an alkenyl group, an alkynyl group, an alkoxy group, an aryloxy group, an aryl group, a heteroaryl group, an amino group, a substituted amino group, a fluorine atom, a group represented by the formula (E-1), a group represented by the formula (E-2), a group represented by the formula (E-3), or the like.

The number of carbon atoms of the heteroaryl group is usually 2 to 60, preferably 4 to 20, more preferably 4 to 10.

The heteroaryl group includes monovalent groups obtained by removing from a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole and dibenzophosphole one of hydrogen atoms linking directly to a carbon atom or a hetero atom constituting the ring of the compound, and monovalent groups obtained by removing from a compound in which the heterocyclic ring itself shows no aromaticity but an aromatic ring is condensed to the heterocyclic ring such as phenoxazine, phenothiazine, dibenzoborole, dibenzosilole and benzopyran one of hydrogen atoms linking directly to a carbon atom or a hetero atom constituting the ring of the compound. A hydrogen atom of these groups are optionally substituted with an alkyl group, an alkenyl group, an alkynyl group, an alkoxy group, an aryloxy group, an aryl group, a heteroaryl group, an amino group, a substituted amino group, a fluorine atom, a group represented by the formula (E-1), a group represented by the formula (E-2), a group represented by the formula (E-3), or the like.

The explanations of the heteroaryl group described above are equally applicable in the present specification.

The number of carbon atoms of the heteroarylene group, not including the number of carbon atoms of a substituent, is usually 2 to 60, preferably 3 to 20, more preferably 4 to 15.

The heteroarylene group includes divalent groups obtained by removing from a heterocyclic compound such as pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two of hydrogen atoms linking directly to a carbon atom or a hetero atom constituting the ring. A hydrogen atom of these groups are optionally substituted with an alkyl group, an alkenyl group, an alkynyl group, an alkoxy group, an aryloxy group, an aryl group, a heteroaryl group, an amino group, a substituted amino group, a fluorine atom, a group represented by the formula (E-1), a group represented by the formula (E-2), a group represented by the formula (E-3), or the like.

The above-mentioned organometal group is a group obtained by removing from a metal complex having a carbon-metal bond one or two hydrogen atoms.

The organometal group includes groups obtained by removing from a compound represented by the formula (U) one or two hydrogen atoms linking directly to a carbon atom or a hetero atom, and the like.

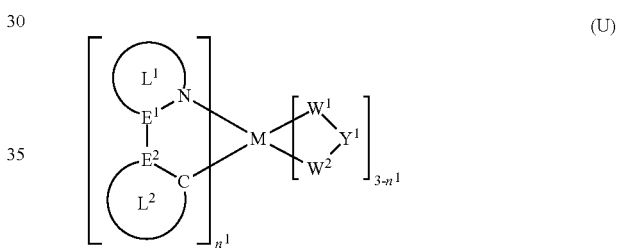

(U)

[wherein,

M represents a ruthenium atom, a rhodium atom or an iridium atom.

$n^1$ represents an integer of 1 to 3.

$E^1$ and $E^2$ each independently represent a carbon atom or a nitrogen atom, provided that at least one of $E^1$ and $E^2$ is a carbon atom.

The ring $L^1$ represents an aromatic heterocyclic ring which optionally have a substituent. When there are a plurality of the substituents, they may be the same or different and may be combined together to form a ring together with an atom to which they are attached. When there are a plurality of rings $L^1$, they may be the same or different.

The ring $L^2$ represents an aromatic hydrocarbon ring which optionally have a substituent or an aromatic heterocyclic ring which optionally have a substituent. When there are a plurality of the substituents, they may be the same or different and may be combined together to form a ring together with an atom to which they are attached. When there are a plurality of rings $L^2$, they may be the same or different.

$W^1$—$Y^1$—$W^2$ represents an anionic bidentate ligand. $W^1$ and $W^2$ each independently represent a carbon atom, an oxygen atom or a nitrogen atom and these atoms may be an atom constituting the ring. $Y^1$ represents a single bond or an atomic group constituting a bidentate ligand together with $W^1$ and $W^2$. When there are a plurality of $W^1$—$Y^1$—$W^2$, they may be the same or different.].

The compound represented by the formula (U) is constituted of a central metal M, a ligand of which number is ruled by a suffix $n^1$ and a ligand of which number is ruled by a suffix 3-$n^1$.

M is preferably an iridium atom or a rhodium atom, more preferably an iridium atom.

It is preferable that $E^1$ and $E^2$ are a carbon atom.

The aromatic heterocyclic ring represented by the ring $L^1$ may be a monocyclic ring or a condensed ring, and includes preferably a pyridine ring, a pyrimidine ring, an imidazole ring and a triazole ring. These rings optionally have a substituent.

The aromatic hydrocarbon ring and the aromatic heterocyclic ring represented by the ring $L^2$ may be a monocyclic ring or a condensed ring, and includes preferably a benzene ring, a naphthalene ring, a fluorene ring, a phenanthrene ring, a pyridine ring, a diazabenzene ring and a triazine ring, more preferably a benzene ring, a pyridine ring and a pyrimidine ring. These rings optionally have a substituent.

The substituent which the ring $L^1$ and the ring $L^2$ optionally have includes an alkyl group, an alkoxy group, an aryl group, an aryloxy group, a heteroaryl group, a fluorine atom, a substituted amino group and the like.

At least one ring selected from the group consisting of the ring $L^1$ and the ring $L^2$ preferably has an aryl group which optionally have a substituent, a heteroaryl group which optionally have a substituent or a substituted amino group which optionally have a substituent (hereinafter, these three kinds of substituents are collectively called "group A of substituent" in some cases), more preferably has an aryl group which optionally have a substituent.

It is preferable that the group A of substituent is a dendron.

The anionic bidentate ligand represented by $W^1$—$Y^1$—$W^2$ includes, for example, ligands shown below.

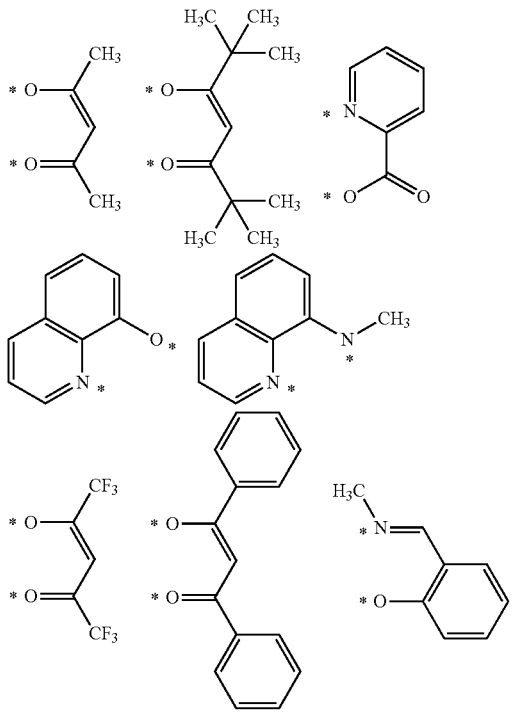

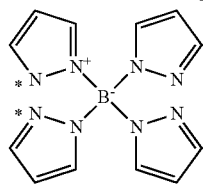

[wherein, * represents a site linking to M.].

The above-mentioned aliphatic hydrocarbon group includes an alkyl group, alkenyl group, alkynyl group and the like.

The alkyl group may be any of linear, branched and cyclic. The number of carbon atoms of the linear alkyl group is usually 1 to 50, preferably 3 to 30, more preferably 4 to 20. The number of carbon atoms of the branched or cyclic alkyl group is usually 3 to 50, preferably 3 to 30, more preferably 4 to 20.

The alkyl group optionally have a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group, a dodecyl group and a cyclohexyl group and groups obtained by substituting a hydrogen atom of these groups with an alkoxy group, an aryl group, a heteroaryl group, an amino group, a substituted amino group, a fluorine atom or the like, and examples thereof include a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-dihexylphenyl)propyl group, a 6-ethyloxyhexyl group, a cyclohexyl group, a cyclohexylmethyl group and a cyclohexylethyl group.

The explanations of the alkyl group described above are equally applicable in the present specification.

The alkenyl group may be any of linear, branched and cyclic. The number of carbon atoms of the linear alkenyl group, not including the number of carbon atoms of a substituent, is usually 2 to 30, preferably 3 to 20. The number of carbon atoms of the branched or cyclic alkenyl group, not including the number of carbon atoms of a substituent, is usually 3 to 30, preferably 4 to 20.

The alkenyl group optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group and a 7-octenyl group, and these groups carrying a substituent.

The alkynyl group may be any of linear, branched and cyclic. The number of carbon atoms of the alkynyl group, not including the number of carbon atoms of a substituent, is usually 2 to 20, preferably 3 to 20. The number of carbon atoms of the branched or cyclic alkynyl group, not including the number of carbon atoms of a substituent, is usually 4 to 30, preferably 4 to 20.

The alkynyl group optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group and a 5-hexynyl group, and these groups carrying a substituent.

The substituent which the above-described aromatic group, the above-described organometal group or the above-described aliphatic hydrocarbon group has includes alkyl groups such as a methyl group, an ethyl group, a n-propyl group, an isopropyl group, a n-butyl group, an isobutyl group, a tert-butyl group, a n-pentyl group, an isoamyl group, a 2-ethylbutyl group, a n-hexyl group, a cyclohexyl group, a n-heptyl group, a cyclohexylmethyl group, a cyclohexylethyl group, a n-octyl group, a 2-ethylhexyl group, a 3-n-propylheptyl group, a n-decyl group, a 3,7-dimethyloctyl group, a 2-ethyloctyl group, a 2-n-hexyldecyl group and a n-dodecyl group; alkyl groups which optionally have a substituent such as a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexylphenyl)propyl group and a 6-ethyloxyhexyl group; an alkenyl group, an alkynyl group, an alkoxy group, an aryloxy group, an aryl group, a heteroaryl group, a fluorine atom, a group represented by the formula (E-1), a group represented by the formula (E-2), a group represented by the formula (E-3) and the like.

$R^1$ includes a phenyl group, a naphthyl group, an anthracenyl group, a phenanthryl group, an indenyl group, a fluorenyl group, a pyrenyl group, a pyridyl group, a quinazolyl group, a quinolyl group, a pyrimidyl group, a furyl group, a thienyl group, a pyrrolyl group, an imidazolyl group, a tetrazolyl group, a 1-propenyl group, a cyclohexenyl group, a cyclopentenyl group, a 1,4-benzoquinyl group, a 6-oxo-1-cyclohexenyl group, a 5-oxo-1-cyclopentenyl group and the like.

$X^1$ represents Cl, Br, I or —O—S(=O)$_2$R$^{C1}$ (wherein, R$^{C1}$ represents an alkyl group or an aryl group and these groups optionally have a substituent), preferably Cl, Br, a mesylate group or a trifluoromethanesulfonate group, more preferably Cl or Br, further preferably Br.

The compound (1) includes 1-bromooctane, 1-iodocyclohexane, 1-iodopentene, 1,4-dibromoisopentane, benzyl chloride, phenyl bromide, o-tolyl bromide, p-tert-butylphenyl bromide, 2,6-dimethylphenyl bromide, 3,5-dimethylphenyl bromide, 2-hydroxyethylphenyl bromide, 4-cyclohexylphenyl bromide, 3-bromobenzo trifluoride, β-bromostyrene, 3-bromo-4-chlorobenzo trifluoride, 2-naphthyl bromide, 9,10-dibromoanthracene, 9-bromoanthracene, 1,3-dibromobenzene, m-methoxyphenyl bromide, 4-bromobenzaldehyde, 1,4-dibromo-2-fluorobenzene, methyl 2-bromophenylacetate, methyl 3-bromophenylacetate, ethyl 4-bromophenylacetate, methyl 3-bromocinnamate, methyl 5-bromo salicylate, 4-bromobenzamide, 4-bromobenzonitrile, 9-bromophenanthrene, 2-bromofluorene, 5-bromoindanone, 2,7-dibromofluorene, 2,7-dibromo-9,9-dioctylfluorene, bis(4-bromophenyl)[4-(methylpropyl)phenyl]amine, 2,7-dibromo-9,9-bis[3-ethoxycarbonyl-4-[2-[2-(2-methoxyethoxy)ethoxy]ethoxy]phenyl]-fluorene, 2,7-dibromo-9,9-bis(3-phenyl)fluorene, N,N'-bis(4-bromophenyl)-N,N'-bis(4-butyl-2,6-dimethylphenyl)-1,4-phenylenediamine, bis(4-bromophenyl)-N,N'-bis(4-methylphenyl)-9,10-anthracenediamine, 3,7-dibromo-N-(4-butylphenyl)phenoxazine, a compound (1-8) described later, 6-bromo-2-naphthol, 4,4'-dibromobiphenyl, 2-pyridyl bromide, 2-bromofuran, 3-bromofuran, 2-bromothiophene, 4-bromopyrazole, 2-bromothiazole-2-methyl-5-bromobenzooxazole, 2-methyl-5-bromobenzothiazole, 5-bromouracil, 8-bromoquinoline, 4-bromoisoquinoline, 1-benzyl-5-bromotetrazole, phenyl chloride, o-tolyl chloride, 3-chlorotoluene, 4-chlorotoluene, 2-chloroacetophenone, 4-chloroacetophenone, p-tert-butylphenyl chloride, 2,6-dimethylphenyl chloride, 3,5-dimethylphenyl chloride, 4-cyclohexylphenyl chloride, 2-chloro-4-fluorotoluene, 1-chloro4-nitrobenzene, methyl 2-chlorophenylacetate, methyl 3-bromophenylacetate, ethyl 4-chlorophenylacetate, 3-chlorobenzophenone, 4-chloro-1-naphthol, 4-chloroaniline, 4-chloro-N,N'-dimethylaniline, 4-chloro-N,N'-diphenylaniline, 5-chloro-N,N'-dimethylaniline, 5-chloro-2-methoxyaniline, 4-chlorobenzoic acid, methyl 3-chlorobenzoate, phenyl 2-chlorobenzoate, 2-chloroacetamide, 4-chloroacetamide, 2-chlorobenzyl cyanide, 2-naphthyl chloride, 9,10-dichloroanthracene, 9-chloroanthracene, 1,3-dichlorobenzene, o-methoxyphenyl chloride, m-methoxyphenyl chloride, p-methoxyphenyl chloride, 3,5-dimethoxychlorotoluene, 3-chlorobenzonitrile, 2,7-dichlorobenzaldehyde, 1,4-dichloro-2-fluorobenzene, 2-pyridyl chloride, 2-chloro-6-trifluoropyridine, 1-(3-chlorophenyl)-3-methyl-2-pyrazolin-5-one, 3-chlorothiophene, 5-chloro-1-methylimidazole, 5-chloro-1-methylbenzotriazole, 2-chloroindole, 2-chlorobenzoimidazole, 8-chloro-5-methoxyquinoline, 2-chlorobenzoxazole, 2-methyl-5-chlorobenzooxazole, 2-methyl-5-chlorobenzothiazole-2,6-dichloropyridine, 3,5-dichloropyridine, 2-chlorobenzothiazole, 6-chloropurine, 2-chloropyrazine, 1,4-dichlorophthalazine, 2,4-chloropyrimidine, phenyl iodide, o-tolyl iodide, p-tert-butylphenyl iodide, 2,6-dimethylphenyl iodide, 3,5-dimethylphenyl iodide, 4-iodoacetophenone, 2-iodobenzoic acid, 2-naphthyl iodide, 9,10-diiodoanthracene, 1,3-diiodobenzene, m-methoxyphenyl iodide, N-tert-butoxycarbonyl-4-iodophenylalaninemethyl ester, 4,4'-diiodobiphenyl, 2-methyl-5-iodo-benzooxazole, 2-methyl-5-iodo-benzothiazole, 1,4-diiodo-2-fluorobenzene, 2-pyridyl iodide, vinyl chloride, vinyl bromide, 1,2-ethylene dichloride, allyl chloride, allyl bromide, cyclohexen-1-yl bromide, cyclopentene-1-yl chloride, 2-methyl-5-(p-toluenesulfonate)-benzooxazole, 2-methyl-5-(p-toluenesulfonate)-benzothiazole-2-pyridyltrifluoromethanesulfonate, 1,1'-bi-2-naphtholbis(trifluoromethanesulfonate), 1,2,2-trimethylvinyl trifluoromethanesulfonate, cyclohexen-1-yl-trifluoromethanesulfonate, 2-methyl-5-trifluoromethanesulfonate benzooxazole, 2-methyl-5-trifluoromethanesulfonate benzothiazole, 4-bromophenyl trifluoromethanesulfonate, 2-methyl-5-methanesulfonate benzooxazole, 2-methyl-5-methanesulfonate benzothiazole, phenyldiazonium tetrafluoroborate salt and the like.

The compound (1) may be a commercially available or can be produced according to any known methods.

The use amount of the compound (1) is usually 0.1 to 10 mol, preferably 0.2 to 5 mol, more preferably 0.4 to 3 mol, particularly preferably 0.5 to 2 mol, with respect to 1 mol of the compound (2).

The compounds (1) may be used singly or in combination with each other.

<Compound (2) Having One or Two Boron Atom-Containing Leaving Groups>

The compound (2) having one or two boron atom-containing leaving groups (hereinafter, referred to as a compound (2) in some cases) is usually an organic compound having a molecular weight of 5000 or less and having one or two boron atom-containing leaving groups, and it is a compound dissolvable in an organic solvent.

The boron atom-containing leaving group of the compound (2) is a group which leaves by reacting with the compound (1) having one or two leaving groups in the coupling reaction such as a cross coupling reaction in the present invention.

The leaving group includes leaving groups represented by B(R$^{C2}$)$_2$, B(OR$^{C2}$)$_2$, BF$_3$T and the like. R$^{C2}$ represents a hydrogen atom, an alkyl group or an aryl group, and the alkyl group and the aryl group optionally have a substituent. The $R^{C2}$s may be the same or different and they may be combined together to form a ring together with the boron atom to which they are attached or together with the oxygen atoms to which they are attached and the boron atom to which the oxygen atoms are attached. T represents Li, Na, K, Rb or Cs.

The leaving group represented by $B(R^{C2})_2$ includes a group represented by the following formula (G-1), and the like.

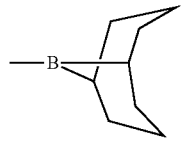
(G-1)

The leaving group represented by $B(OR^{C2})_2$ includes $B(OH)_2$, $B(OCH_3)_2$, $B(OCH_2CH_3)_2$, a group represented by the formula (G-1), a boronic acid ethylene glycol ester (namely, a group represented by the formula (G-2)), a boronrc acid pinacol ester (namely, a group represented by the formula (G-3)), a boronic acid trimethylene glycol ester (namely, a group represented by the formula (G-4)), a boronic acid catechol ester (namely, a group represented by the formula (G-5)), a boronic acid trimer anhydride (namely, a group obtained by removing from boronic acid trimer anhydride one hydrogen atom on a boron atom) and the like, usually, $B(OH)_2$, $B(OCH_3)_2$, $B(OCH_2CH_3)_2$, a boronic acid ethylene glycol ester, a boronic acid pinacol ester, a boronic acid trimethylene glycol ester, a boronic acid catechol ester, a boronic acid trimer anhydride and the like, preferably a boronic acid pinacol ester and a boronic acid catechol ester, more preferably a boronic acid pinacol ester.

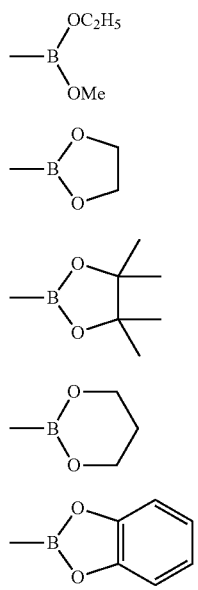

The compound (2) is preferably a compound represented by the formula (B) (hereinafter, referred to as a compound (B) in some cases).

$$R^2\text{---}(X^2)_m \quad (B)$$

[wherein, $R^2$ represents an organic group. $X^2$ represents $B(R^{C2})_2$, $B(OR^{C2})_2$ or $BF_3T$, wherein $R^{C2}$ represents a hydrogen atom, an alkyl group or an aryl group and these groups optionally have a substituent, and the $R^{C2}$s may be the same or different and they may be combined together to form a ring together with the boron atom to which they are attached or together with the oxygen atoms to which they are attached and the boron atom to which the oxygen atoms are attached, and T represents Li, Na, K, Rb or Cs. m represents 1 or 2.].

The organic group represented by $R^2$ includes the same groups as represented by $R^1$.

$X^2$ is preferably $B(OR^{C2})_2$.

The group represented by $B(R^{C2})_2$ includes the same leaving groups as represented by the above-described $B(R^{C2})_2$.

The group represented by $B(OR^{C2})_2$ includes the same leaving groups as represented by the above-described $B(OR^{C2})_2$.

The compound (2) includes propylboronic acid, (2-methylpropyl)boronic acid, s-butylboronic acid, (E)-1-pentenylboronic acid, n-octylboronic acid, cyclopentylboronic acid, trans-4,4,5,5-tetramethyl-2-(1-octenyl)-1,3,2-dioxaborolane, 2-cyclohexyl-4,4,5,5-tetramethyl-1,3,2-dioxaborolane, 2-benzyl-4,4,5,5-tetramethyl-1,3,2-dioxaborolane, phenylboronic acid, 2-methylphenylboronic acid, 3-methylphenylboronic acid, 4-methylphenylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9,9-dioctyl-2-(4,4,5,5-tetramethyl-1,3,2-dioxaborolan-2-yl)fluorene, 9-phenanthrenylboronic acid, 9-anthracenylboronic acid, 9,9-dimethyl-2-fluoreneboronic acid, 9,9'-spirobi(fluoren-2-yl)boronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 2,6-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-dimethylamino)phenylboronic acid, 3-(N,N-diethylamino)

phenylboronic acid, 4-(N,N-diethylamino)phenylboronic acid, 4-(diphenylamino)phenylboronic acid, furan-2-boronic acid, furan-3-boronic acid, 2-formylfuranboronic acid, 3-formylfuran-2-boronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 3-formylthiophene-2-boronic acid, 5-methylthiophene-2-boronic acid, benzothiophene-2-boronic acid, dibenzothiophene-4-boronic acid, pyrazole-4-boronic acid, 3-methylpyrazole-4-boronic acid, 3,5-dimethylpyrazole-4-boronic acid, 3-nitro-1,2,4-triazole-5-boronic acid, thiazole-2-boronic acid, pyridine-3-boronic acid, pyridine-4-boronic acid, pyrimidine-5-boronic acid, quinolone-8-boronic acid, isoquinoline-4-boronic acid, 1,4-bis(4,4,5,5-tetramethyl-1,3,2-dioxaborolan-2-yl)benzene, 1,3-bis(4,4,5,5-tetramethyl-1,3,2-dioxaborolan-2-yl)benzene, 1,3,5-tris(4,4,5,5-tetramethyl-1,3,2-dioxaborolan-2-yl)benzene, 9,9-dimethyl-2,7-bis(4,4,5,5-tetramethyl-1,3,2-dioxaborolan-2-yl)fluorene, 4-(4,4,5,5-tetramethyl-1,3,2-dioxaborolan-2-yl)biphenyl, 2,7-bis(4,4,5,5-tetramethyl-1,3,2-dioxaborolan-2-yl)-9,9-dioctylfluorene, 2,7-bis(4,4,5,5-tetramethyl-1,3,2-dioxaborolan-2-yl)-9,9-bis[3-ethoxycarbonyl-4-[2-[2-(2-methoxyethoxy)ethoxy]ethoxy]phenyl]-fluorene, 2,7-bis(4,4,5,5-tetramethyl-1,3,2-dioxaborolan-2-yl)-9,9-bis[4-(hexyl)phenyl]-fluorene, 9,10-bis(4,4,5,5-tetramethyl-1,3,2-dioxaborolan-2-yl)anthracene, 1,2-bis(4,4,5,5-tetramethyl-1,3,2-dioxaborolan-2-yl)stilbene and the like.

The compound (2) may be commercially available or can be produced according to any know methods.

As the combination of the compound (1) with the compound (2), a combination of a compound (A) in which $R^1$ is an aromatic group which optionally have a substituent and $X^1$ is Br with a compound (B) in which $R^2$ is an aromatic group which optionally have a substituent and $X^2$ is a boronic acid pinacol ester is particularly preferable.

The compounds (2) may be used singly or in combination with each other.

<Organic Base (P)>

The organic base (P) in the present invention is a strongly basic organic compound, preferably an organic compound having a pKa of 11 or more. Further, it is preferably a hydrophilic compound.

The organic base (P) includes ammonium hydroxide compounds, ammonium carbonate compounds, ammonium bicarbonate compounds, boronic acid ammonium compounds, 1,5-diazabicyclo[4,3,0]non-5-ene (DBN), 1,8-diazabicyclo[5.4.0]undec-7-ene (DBU), guanidine and the like.

The organic base (P) is preferably an organic base having 4 to 15 carbon atoms, more preferably an ammonium hydroxide compound having 4 to 15 carbon atoms, an ammonium carbonate compound having 4 to 15 carbon atoms or an ammonium bicarbonate compound having 4 to 15 carbon atoms, further preferably an ammonium hydroxide compound having 4 to 15 carbon atoms, particularly preferably a tetraalkylammonium hydroxide having 4 to 8 carbon atoms. Further, the above-mentioned ammonium hydroxide compound, ammonium carbonate compound and ammonium bicarbonate compound are preferably a quaternary ammonium compound. Such compounds are preferable because they have high versatility and show high reactivity.

The ammonium hydroxide compound includes $(CH_3)_4NOH$ (tetramethylammonium hydroxide), $(C_2H_5)_4NOH$ (tetraethylammonium hydroxide), $(C_3H_7)_4NOH$ (tetrapropylammonium hydroxide), $(PhCH_2)(CH_3)_3NOH$ (benzyltrimethylammonium hydroxide), $(C_4H_9)_4NOH$ (tetrabutylammonium hydroxide), $(Ph)(CH_3)_3NOH$ (phenyltrimethylammonium hydroxide), $(C_5H_{11})_4NOH$, $(C_{16}H_{33})(CH_3)_3NOH$, $(C_{16}H_{33})(CH_3)_3NOH$, $(C_8H_{17})_3(CH_3)NOH$, $(C_8H_{17})_2(C_{10}H_{21})(CH_3)NOH$, $(C_8H_{17})(C_{10}H_{21})_2(CH_3)NOH$, $(C_{10}H_{21})_3(CH_3)NOH$, $(C_8H_{17})_4NOH$, benzyltriethylammonium hydroxide and the like.

The ammonium carbonate compound includes $[(CH_3)_4N]_2CO_3$ (tetramethylammonium carbonate), $[(C_2H_5)_4N]_2CO_3$ (tetraethylammonium carbonate), $[(C_3H_7)_4N]_2CO_3$ (tetrapropylammonium carbonate), $[(PhCH_2)(CH_3)_3N]_2CO_3$ (benzyltrimethylammonium carbonate), $[(C_4H_9)_4N]_2CO_3$ (tetrabutylammonium carbonate), $[(Ph)(CH_3)_3N]_2CO_3$ (phenyltrimethylammonium hydroxide) and the like.

The ammonium bicarbonate compound includes $(CH_3)_4NCO_3H$ (tetramethylammonium bicarbonate), $(C_2H_5)_4NCO_3H$ (tetraethylammonium bicarbonate), $(C_3H_7)_4NCO_3H$ (tetrapropylammonium bicarbonate), $(PhCH_2)(CH_3)_3NCO_3H$ (benzyltrimethylammonium bicarbonate), $(C_4H_9)_4NCO_3H$ (tetrabutylammonium bicarbonate), $(Ph)(CH_3)_3NCO_3H$ (phenyltrimethylammonium bicarbonate) and the like.

The boronic acid ammonium compound includes $(CH_3)_4NArB(OH)_3$ (tetramethylammonium aryl boronate), $(C_2H_5)_4NArB(OH)_3$ (tetraethylammonium aryl boronate), $(C_3H_7)_4NArB(OH)_3$ (tetrapropylammonium aryl boronate), $(PhCH_2)(CH_3)_3ArB(OH)_3$ (benzyltrimethylammonium aryl boronate), $(C_4H_9)_4NArB(OH)_3$ (tetrabutylammonium aryl boronate), $(Ph)(CH_3)_3NArB(OH)_3$ (phenyltrimethylammonium aryl boronate) and the like. The above-mentioned aryl group (Ar) which the boronic acid ammonium compound has includes a phenyl group, a 1-naphthyl group, a 2-naphthyl group and the like. A hydrogen atom of these groups optionally be substituted with an alkyl group, an alkoxy group, an aryl group, a fluorine atom or the like.

The use amount of the organic base (P) is usually 0.5 to 100 mol, preferably 0.5 to 70 mol, more preferably 0.5 to 40 mol, further preferably 0.9 to 20 mol, particularly preferably 2 to 10 mol, with respect to 1 mol of the total amount of the compound (1) and the compound (2).

<Organic Base (Q)>

The organic base (Q) in the present invention is an organic base having a larger number of carbon atoms than the above-described organic base (P), and is a strongly basic organic compound. It is preferably an organic compound having a pKa of 11 more, and is preferably a hydrophilic compound.

When three or more organic bases are used in the method for producing a compound of the present invention, the organic base to be used in the largest substance quantity and an organic base smaller in the number of carbon atoms than that organic base are called organic bases (P), and an organic base larger in the number of carbon atoms than that organic base to be used in the largest substance quantity is called an organic base (Q). When the organic base to be used in the largest substance quantity is the organic base largest in the number of carbon atoms, this organic base is called an organic base (Q) and organic bases other than this organic base are called organic bases (P).

The organic base (Q) includes the same compounds as the organic base (P).

When tetramethylammonium hydroxide and tetraethylammonium hydroxide are used as organic bases in the method for producing a compound of the present invention, tetramethylammonium hydroxide corresponds to the organic base (P) and tetraethylammonium hydroxide corresponds to the organic base (Q). When tetraethylammonium hydroxide and tetrabutylammonium hydroxide are used as organic bases in the method for producing a compound of the present invention, tetraethylammonium hydroxide corresponds to the organic base (P) and tetrabutylammonium hydroxide corresponds to the organic base (Q). That is, tetraethylammonium hydroxide corresponds to the organic base (Q) in the former case, and corresponds to the organic base (P) in the latter case.

The organic base (Q) is preferably an organic base having 16 to 60 carbon atoms, more preferably an ammonium hydroxide compound having 16 to 60 carbon atoms, an ammonium carbonate compound having 16 to 60 carbon atoms or an ammonium bicarbonate compound having 16 to 60 carbon atoms, further preferably an ammonium hydroxide compound having 16 to 60 carbon atoms, particularly preferably a tetraalkylammonium hydroxide having 16 to 24 carbon atoms. Further, the above-mentioned ammonium hydroxide compound, ammonium carbonate compound and ammonium bicarbonate compound are preferably a quaternary ammonium compound. Such compounds are preferable because they have high versatility and show high reactivity.

The use amount of the organic base (Q) is usually 0.001 to 50 mol, with respect to 1 mol of the total amount of the compound (1) and the compound (2). It is preferably 0.005 to 10 mol, more preferably 0.01 to 1 mol, further preferably 0.01 to 0.8 mol, particularly preferably 0.03 to 0.1 mol. The use amount (substance quantity) of the organic base (Q) is preferably smaller than the use amount (substance quantity) of the organic base (P).

<Phase Transfer Catalyst>

The phase transfer catalyst in the present invention is one transferring between an aqueous phase and an oil phase to transport a reaction reagent from one phase to another phase, thereby promoting the reaction.

It is preferable that the phase transfer catalyst has a larger number of carbon atoms than the organic base (P). For example, when $(CH_3)_4NOH$ (tetramethylammonium hydroxide) having 4 carbon atoms is used as the organic base (P) in the present invention, it is preferable, for example, that $(C_4H_9)_4NBr$ (tetrabutylammonium bromide) having 16 carbon atoms is used as the phase transfer catalyst.

The phase transfer catalyst includes ammonium compounds, macrocyclic polyethers and the like, preferably ammonium compounds, more preferably ammonium compounds having 16 to 60 carbon atoms, further preferably quaternary ammonium compounds having 16 to 60 carbon atoms, particularly preferably quaternary ammonium halides having 16 to 60 carbon atoms, especially preferably tetraalkylammonium halides having 16 to 24 carbon atoms. Such compounds are preferable because they have high function as the phase transfer catalyst.

The above-described ammonium compound includes $(C_4H_9)_4NF$ (tetrabutylammonium fluoride), $(C_4H_9)_4NCl$ (tetrabutylammonium chloride), $(C_4H_9)_4NBr$ (tetrabutylammonium bromide), $(C_4H_9)_4NI$ (tetrabutylammonium iodide), $(C_5H_{11})_4NF$ (tetrapentylammonium fluoride), $(C_5H_{11})_4NCl$ (tetrapentylammonium chloride), $(C_5H_{11})_4NBr$ (tetrapentylammonium bromide), $(C_5H_{11})_4NI$ (tetrapentylammonium iodide), $(C_{16}H_{33})(CH_3)_3NCl$, $(C_8H_{17})_3(CH_3)NCl$, $(C_8H_{17})_2(C_{10}H_{21})(CH_3)NCl$, $(C_8H_{17})(C_{10}H_{21})_2(CH_3)NCl$, $(C_{10}H_{21})_3(CH_3)NCl$, $(C_8H_{17})_4NBr$, benzyltriethylammonium chloride, cetylpyridinium chloride and the like, preferably, $(C_4H_9)_4NF$, $(C_4H_9)_4NCl$, $(C_4H_9)_4NBr$, $(C_4H_9)_4NI$, $(C_5H_{11})_4NCl$, $(C_5H_{11})_4NBr$, $(C_5H_{11})_4NI$, $(C_{16}H_{33})(CH_3)_3NCl$, $(C_8H_{17})_3(CH_3)NCl$, $(C_8H_{17})_2(C_{10}H_{21})(CH_3)NCl$, $(C_8H_{17})(C_{10}H_{21})_2(CH_3)NCl$, $(C_{10}H_{21})_3(CH_3)NCl$ and $(C_8H_{17})_4NBr$. The phase transfer catalysts may be used singly or in combination with each other.

The use amount of the phase transfer catalyst is usually 0.001 to 50 mol, with respect to 1 mol of the total amount of the compound (1) and the compound (2). It is preferably 0.005 to 10 mol, more preferably 0.01 to 1 mol.

The use amount of the phase transfer catalyst with respect to 100 parts by mass of the sum of the organic base (P) and the organic base (Q) is usually 0.01 to 1000 parts by mass, preferably 0.1 to 100 parts by mass, more preferably 1 to 10 parts by mass.

<Organic Solvent>

In the method for producing a compound of the present invention, an organic solvent is usually used. The organic solvent includes aromatic hydrocarbon solvents such as toluene, xylene and mesitylene; ether solvents such as tetrahydrofuran, 1,4-dioxane and dimethoxyethane; amide solvents such as N,N-dimethylacetamide and N,N-dimethylformamide; alcohol solvents such as methanol, ethanol, ethylene glycol, isopropyl alcohol, propylene glycol, methylcellosolve and butylcellosolve; ketone solvents such as acetone, methyl ethyl ketone, cyclopentanone, cyclohexanone, methyl amyl ketone, methyl isobutyl ketone and N-methyl-2-pyrrolidinone; aliphatic hydrocarbon solvents such as pentane, hexane and heptane; nitrile solvents such as acetonitrile; halogenated hydrocarbon solvents such as chloroform; and the like. As the organic solvent, those immiscible with water at any ratio are preferable. Specifically, aromatic hydrocarbon solvents and ether solvents are preferable, and toluene, xylene and mesitylene are more preferable. The organic solvents may be used singly or in combination with each other.

The use amount of the organic solvent is usually 10 parts by mass to 100000 parts by mass, preferably 100 parts by mass to 70000 parts by mass, more preferably 1000 parts by mass to 50000 parts by mass, further preferably 2000 parts by mass to 20000 parts by mass, with respect to 100 parts by mass of the total amount of the compound (1) and the compound (2).

<Water>

In the method for producing a compound of the present invention, water is usually used. The use amount of water is usually 10 parts by mass to 100000 parts by mass, preferably 100 parts by mass to 70000 parts by mass, more preferably 1000 parts by mass to 50000 parts by mass, further preferably 2000 parts by mass to 20000 parts by mass, with respect to 100 parts by mass of the total amount of the compound (1) and the compound (2).

<Transition Metal Catalyst>

As the transition metal catalyst, group 10 transition metal catalysts are preferable. The group 10 transition metal catalyst includes a 0-valent or divalent nickel catalyst, a palladium catalyst, a platinum catalyst and the like, preferably a palladium catalyst.

The palladium catalyst includes dichlorobis(triphenylphosphine)palladium, dichlorobis[tris(2-methoxyphenyl)phosphine]palladium, palladium[tetrakis(triphenylphosphine)], [tris(dibenzylideneacetone)]dipalladium, dichlorobis[dicyclopentyl(2-methoxyphenyl)phosphine]palladium, palladium acetate, dichlorobis[dicyclopentyl(2,6-dimethoxyphenyl)phosphine]palladium and bis[di-tert-butyl (3,5-di-tert-butylphenyl)phosphine]dichloropalladium, and complexes composed of these palladium catalysts further having a ligand such as triphenylphosphine, tri(tert-butyl-phosphine), tricyclohexylphosphine, diphenylphosphinopropane and bipyridyl, and the like, preferably, dichlorobis(triphenylphosphine)palladium and palladium[tetrakis (triphenylphosphine)]. The transition metal catalysts may be used singly or in combination with each other.

The use amount of the transition metal catalyst is usually 0.00001 to 3 mol, preferably 0.0001 to 0.5 mol, with respect to 1 mol of the total amount of the compound (1) and the compound (2).

<Compound>

In the present invention, when a compound (1) having one leaving group and a compound (2) having one leaving group undergo a coupling reaction, a compound in which a residue obtained after leaving of the leaving group of the compound (1) and a residue obtained after leaving of the leaving group of the compound (2) are coupled is usually obtained.

In the present invention, when a compound (1) having one leaving group and a compound (2) having two leaving groups undergo a coupling reaction, a compound in which one residue obtained after leaving of the leaving group of the compound (1) and one residue obtained after leaving of one leaving group of the compound (2) are coupled, or a trimer type compound in which two residues obtained after leaving of the leaving group of the compound (1) and one residue obtained after leaving of two leaving groups of the compound (2) are coupled, is usually obtained.

In the present invention, when a compound (1) having two leaving groups and a compound (2) having one leaving group undergo a coupling reaction, a compound in which one residue obtained after leaving of one leaving group of the compound (1) and one residue obtained after leaving of the leaving group of the compound (2) are coupled, or a trimer type compound in which one residue obtained after leaving of two leaving groups of the compound (1) and two residues obtained after leaving of the leaving group of the compound (2) are coupled, is usually obtained.

Further, in the present invention, when a compound (1) having two leaving groups and a compound (2) having two leaving groups undergo a coupling reaction, a polymer type compound in which one residue obtained after leaving of the leaving groups of the compound (1) and one residue obtained after leaving of the leaving groups of the compound (2) are coupled repeatedly is usually obtained.

In the production method for the present invention, a coupling reaction between a compound (1) having one leaving group and a compound (2) having one leaving group or a coupling reaction between a compound (1) having two leaving groups and a compound (2) having two leaving groups is preferably conducted, and a coupling reaction between a compound (1) having two leaving groups and a compound (2) having two leaving groups is more preferably conducted.

In the present invention, when a compound (A) in which n=1 and a compound (B) in which m=1 are subjected to a coupling reaction, a compound represented by the formula (3a) is usually obtained, when a compound (A) in which n=1 and a compound (B) in which m=2 are subjected to a coupling reaction, a compound represented by the formula (3b) or the formula (3c) is usually obtained, when a compound (A) in which n=2 and a compound (B) in which m=1 are subjected to a coupling reaction, a compound represented by the formula (3d) or the formula (3e) is usually obtained, and when a compound (A) in which n=2 and a compound (B) in which m=2 are subjected to a coupling reaction, a compound having a structure represented by the formula (3f) is usually obtained.

  (3a)

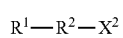  (3b)

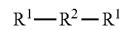  (3c)

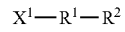  (3d)

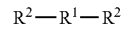  (3e)

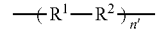  (3f)

[wherein, n' represents the number of a repeating unit.].

In the production method for the present invention, a coupling reaction between a compound (A) and a compound (B) in which n and m are 1 or n and m are 2 is preferably conducted, and a coupling reaction between a compound (A) and a compound (B) in which n and m are 2 is more preferably conducted.

The weight-average molecular weight of the compound having a structure represented by the formula (3f) is usually 1000 to 1000000, preferably 5000 to 500000, more preferably 10000 to 250000. The weight-average molecular weight can be determined by reducing with polystyrene standard using gel permeation chromatography (GPC).

The weight-average molecular weight of the compound having a structure represented by the formula (3f) can be controlled by adjusting the substance quantity ratio of a compound (A) to a compound (B) to be subjected to a coupling reaction.

The compound represented by the formula (3a) includes, specifically,

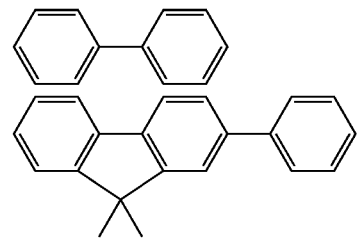

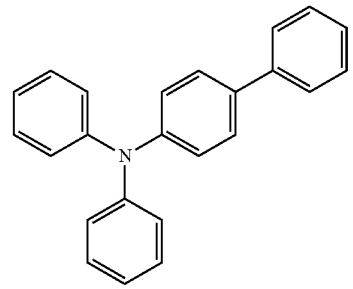
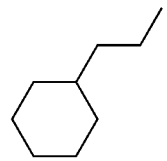

and the like.

The compound represented by the formula (3b) includes, specifically,

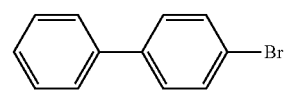

-continued
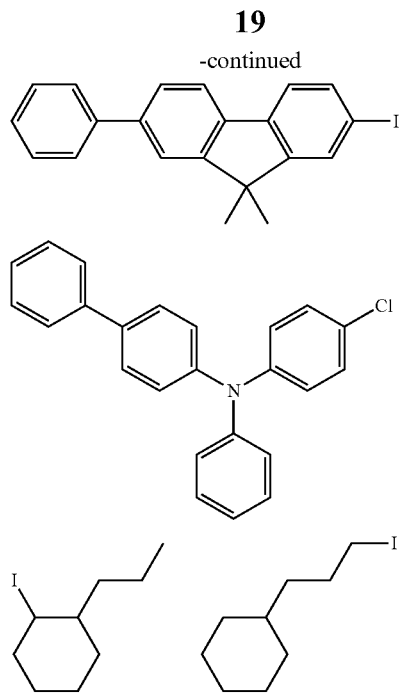
and the like.
The compound represented by the formula (3c) includes, specifically,
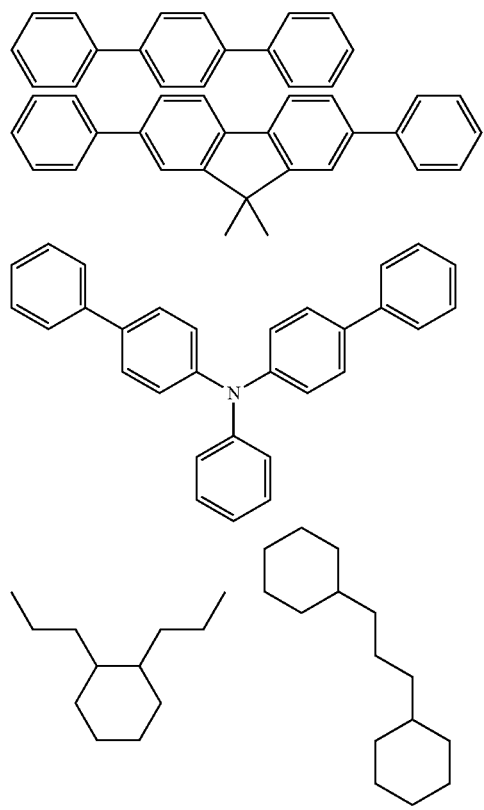
and the like.
The compound represented by the formula (3d) includes, specifically,
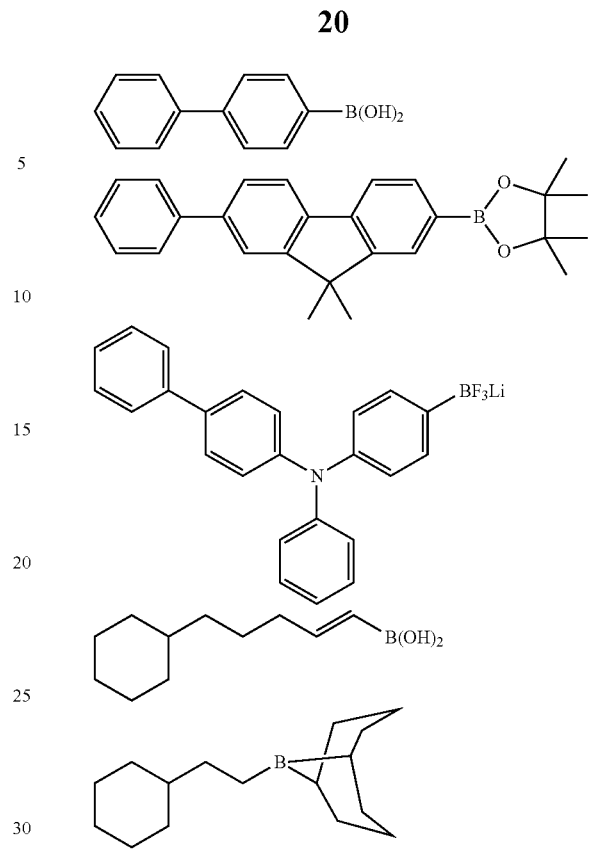
and the like.
The compound represented by the formula (3e) includes, specifically,
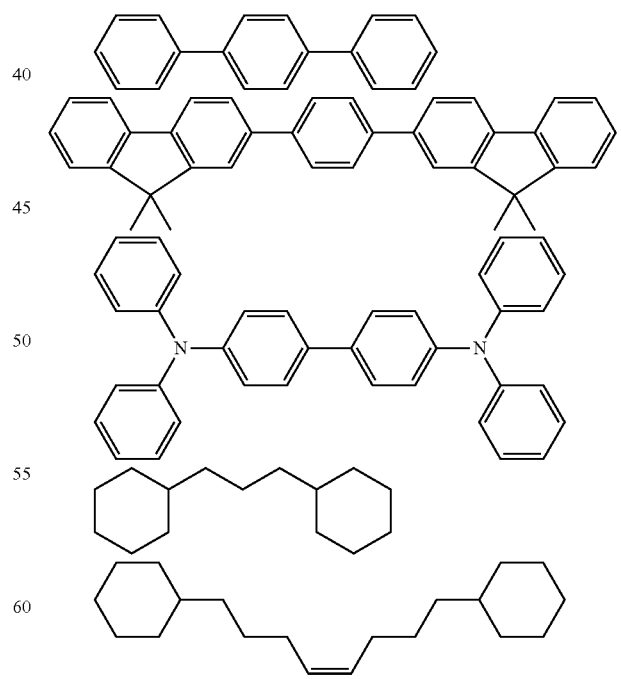
and the like.
The compound having a structure represented by the formula (3f) includes, specifically,

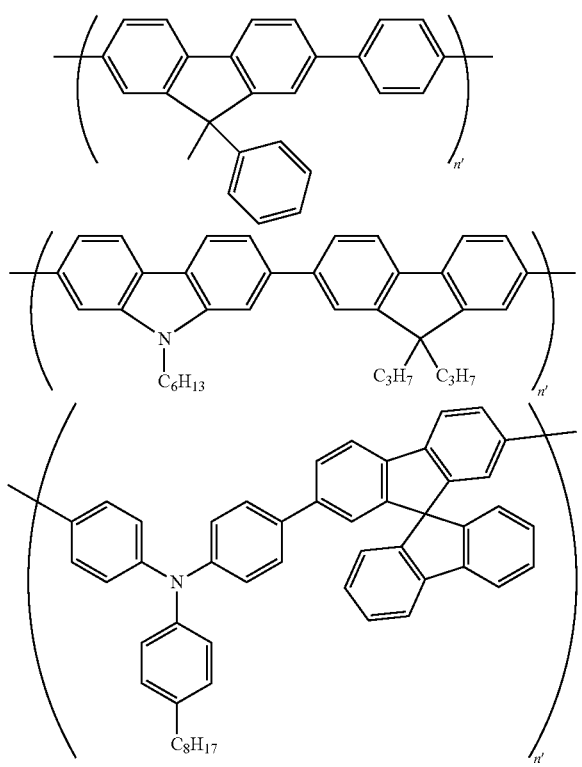

[wherein, n' represents the number of a repeating unit.] and the like.

<Reaction Condition>

The temperature of mixing is usually −100 to 200° C., preferably 0 to 150° C., more preferably 50 to 100° C.

The pressure of mixing is usually atmospheric pressure.

The stirring power of mixing is usually 0.001 to 10 kW/m$^3$, preferably 0.01 to 2 kW/m$^3$, more preferably 0.1 to 1 kW/m$^3$.

The order of mixing is not limited.

After the coupling reaction, a compound can be collected by known methods, such as a method in which the reaction mixture after the coupling reaction and water are mixed and the mixture is separated, a method in which the reaction mixture after the coupling reaction and a lower alcohol such as methanol are mixed and a precipitate deposited is collected by filtration and dried. The collected compound can be purified by known methods such as recrystallization, reprecipitation, continuous extraction by a Soxhlet extractor, column chromatography and sublimation purification.

EXAMPLES

The present invention will be illustrated further in detail by examples below.

<Liquid Chromatography (LC) Analysis Condition>

Measuring apparatus: CBM-20A (manufactured by Shimadzu Corp.)

Column: L-Column2 ODS (3 μm, 4.6 mmφ×25 cm)
Mobile phase A: acetonitrile
Mobile phase B: THF
Mobile phase C: pure water
Gradient: 0.01 minute A=80%, B=0%, C=40%
10 minutes A=60%, B=0%, C=40%
20 minutes A=100%, B=0%, C=0%
100 minutes A=100%, B=0%, C=0%
120 minutes A=0%, B=100%, C=0%
130 minutes A=0%, B=100%, C=0%
Flow rate: 1.0 mL/min
Detection wavelength: 280 nm <Gel Permeation Chromatography (GPC) Analysis Condition>

Measuring apparatus: HLC-822GPC (manufactured by Tosoh Corporation)
Column: PLgel 10 μm MIXED-B (manufactured by Tosoh Corporation)
Column temperature: 40° C.
Mobile phase: tetrahydrofuran
Flow rate: 0.5 mL/min
Detection wavelength: 228 nm Comparative Example 1

Under a nitrogen atmosphere, 4.36 g of a compound (2-1), 3.90 g of a compound (1-1), 0.201 g of phenanthrene (internal standard substance), 0.10 g of benzyltriethylammonium chloride, 31 g of a 28% potassium carbonate aqueous solution and 50 g of toluene were mixed, and further, 0.06 g of palladium[tetrakis(triphenylphosphine)] was added. The resultant mixture was heated at 86° C., and mixed with heating for 1.5 hours at a stirring power of 0.1 kW/m$^3$. The resultant mixture was analyzed by LC, and the reaction yield of the compound (3e-1) was calculated by an internal standard method. The results are shown in Table 1.

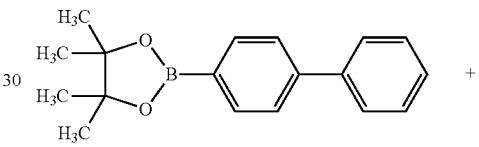

Compound (2-1)

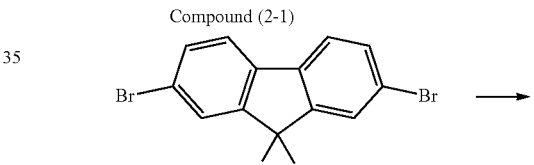

Compound (1-1)

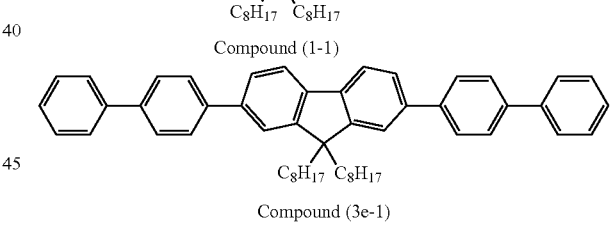

Compound (3e-1)

Compound (2-1): As 4-(4,4,5,5-tetramethyl-1,3,2-dioxaborolan-2-yl)biphenyl, a commercially available product purchased from Tokyo Chemical Industry Co., Ltd. was used.

Compound (1-1): 2,7-dibromo-9,9-dioctylfluorene was synthesized according to WO2002/045184.

Compound (3e-1): 2,7-biphenyl-9,9-dioctylfluorene

Example 1

Under a nitrogen atmosphere, 4.36 g of a compound (2-1), 3.90 g of a compound (1-1), 0.201 g of phenanthrene (internal standard), 0.17 g of tetrabutylammonium bromide, 31 g of a 18% tetramethylammonium hydroxide aqueous solution and 50 g of toluene were mixed, and further, 0.06 g of palladium[tetrakis(triphenylphosphine)] was added. The resultant mixture was heated at 86° C., and mixed with heating for 1.5 hours at a stirring power of 0.1 kW/m$^3$. The resultant mixture was analyzed by LC, and the reaction yield of the compound (3e-1) was calculated by an internal standard method. The results are shown in Table 1.

TABLE 1

|  | organic base (P) | inorganic base | phase transfer catalyst | reaction yield (%) |
|---|---|---|---|---|
| Comparative Example 1 | none | 28% potassium carbonate aqueous | benzyltriethylammonium chloride | 0.1 |
| Example 1 | 18% tetramethylammonium hydroxide aqueous solution | none | tetrabutylammonium bromide | 99 |

The reaction yield of the compound (3e-1) obtained after the reaction of 1.5 hours in Example 1 was higher than the reaction yield of the compound (3e-1) obtained after the reaction of 1.5 hours in Comparative Example 1, teaching that the production method for the present invention gives a higher reaction rate.

Comparative Example 2

Under a nitrogen atmosphere, 2.76 g of a compound (2-2), 2.01 g of a compound (1-2), 1.15 mg of dichlorobis[tris(2-methoxyphenyl)phosphine]palladium and 55 g of toluene were mixed, and the mixture was heated at 86° C. To the resultant mixed liquid was added 30 g of a 10% tetramethylammonium hydroxide aqueous solution, and the mixture was mixed with heating for 1.5 hours at a stirring power of 0.1 kW/m³. The resultant mixture was analyzed by GPC, and the polystyrene-equivalent number-average molecular weight and weight-average molecular weight of the compound (3f-1) were determined. The results are shown in Table 2.

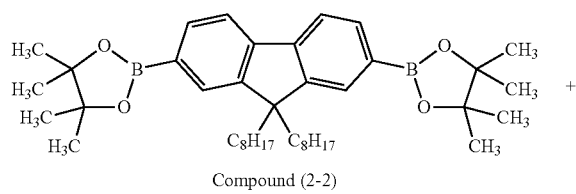

Compound (2-2)

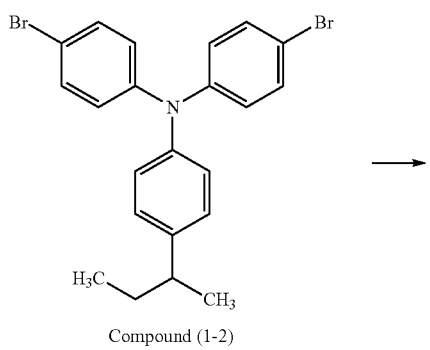

Compound (1-2)

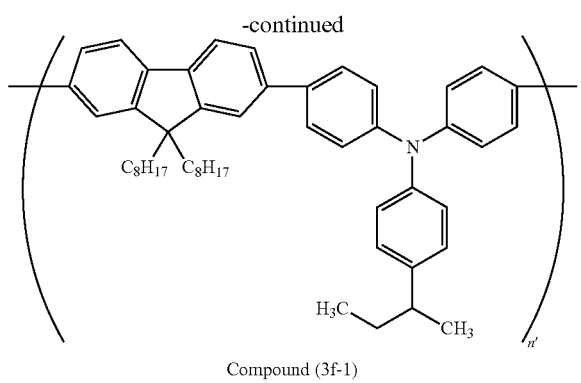

Compound (3f-1)

[wherein, n' represents the number of a repeating unit.]

Compound (2-2): 2,7-bis(4,4,5,5-tetramethyl-1,3,2-dioxaborolan-2-yl)-9,9-dioctylfluorene was synthesized by a method described in U.S. Pat. No. 6,169,163.

Compound (1-2): bis(4-bromophenyl)[4-(methylpropyl)phenyl]amine was synthesized by a method described in WO2002/045184.

Example 2

Under a nitrogen atmosphere, 2.76 g of a compound (2-2), 2.01 g of a compound (1-2), 1.15 mg of dichlorobis[tris(2-methoxyphenyl)phosphine]palladium and 55 g of toluene were mixed, and the mixture was heated at 86° C. To the resultant mixture was added a mixture of 30 g of a 10% tetramethylammonium hydroxide aqueous solution and 0.14 g of tetrabutylammonium bromide, and the mixture was mixed with heating for 1.5 hours at a stirring power of 0.1 kW/m³. The resultant mixture was analyzed by GPC, and the polystyrene-equivalent number-average molecular weight and weight-average molecular weight of the compound (3f-1) were determined. The results are shown in Table 2.

Example 3

Under a nitrogen atmosphere, 2.76 g of a compound (2-2), 2.01 g of a compound (1-2), 1.15 mg of dichlorobis[tris(2-methoxyphenyl)phosphine]palladium and 55 g of toluene were mixed, and the mixture was heated at 86° C. To the resultant mixture was added a mixture of 30 g of a 10% tetramethylammonium hydroxide aqueous solution and 0.21 g of a 55% tetrabutylammonium hydroxide aqueous solution, and the mixture was mixed with heating for 1.5 hours at a stirring power of 0.1 kW/m³. The resultant mixture was analyzed by GPC, and the polystyrene-equivalent number-average molecular weight and weight-average molecular weight of the compound (3f-1) were determined. The results are shown in Table 2.

TABLE 2

|  | organic base (P) | organic base (Q) | phase transfer catalyst | number-average molecular weight | weight-average molecular weight |
|---|---|---|---|---|---|
| Comparative Example 2 | 10% tetramethylammonium hydroxide aqueous solution | none | none | 1000 | 2000 |
| Example 2 | 10% tetramethylammonium hydroxide aqueous solution | none | tetrabutylammonium bromide | 42000 | 135000 |
| Example 3 | 10% tetramethylammonium hydroxide aqueous solution | 55% tetrabutylammonium hydroxide aqueous solution | none | 38000 | 141000 |

The number-average molecular weight and the weight-average molecular weight of the compound (3f-1) obtained after the reaction of 1.5 hours in Examples 2 and 3 were higher than the number-average molecular weight and the weight-average molecular weight of the compound (3f-1) obtained after the reaction of 1.5 hours in Comparative Example 2, teaching that the production method for the present invention gives a higher reaction rate.

Comparative Example 3

Under a nitrogen atmosphere, 3.66 g of a compound (2-3), 3.30 g of a compound (1-3), 0.06 g of dichlorobis(triphenylphosphine)palladium, 1.20 g of methyltrioctylammonium chloride (manufactured by Sigma-Aldrich, trade name: Aliquat336 (registered trademark)) and 52 g of toluene were mixed, and the mixture was heated at 105° C. Into the resultant mixed liquid, 36 g of a 2M sodium carbonate aqueous solution was dropped, and the mixture was mixed with heating for 0.2 hours at a stirring power of 0.01 kW/m$^3$. The resultant mixture was analyzed by GPC, and the polystyrene-equivalent number-average molecular weight and weight-average molecular weight of the compound (3g-1) were determined. The results are shown in Table 3.

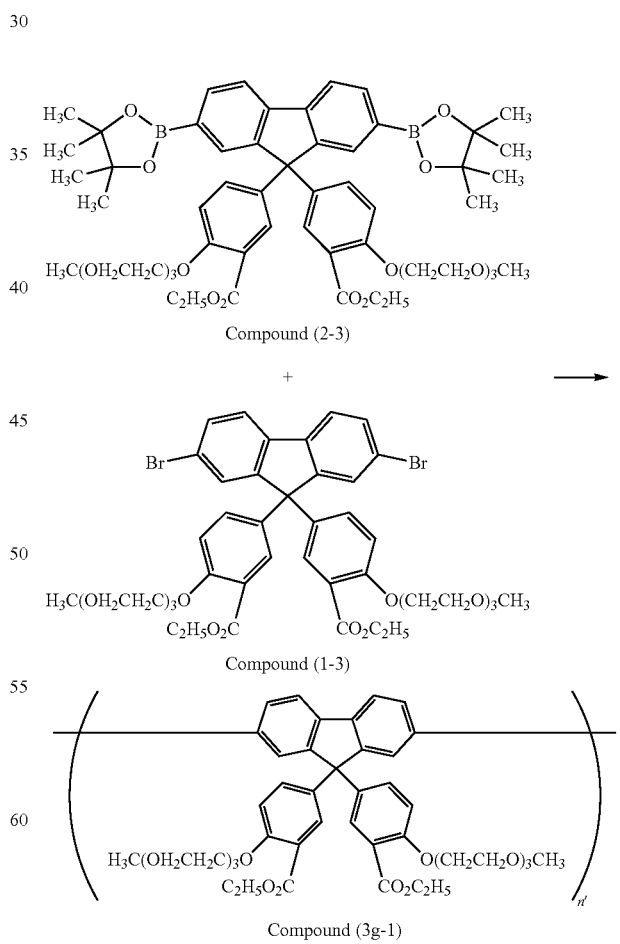

[wherein, n' represents the number of a repeating unit.]

Compound (2-3): 2,7-bis(4,4,5,5-tetramethyl-1,3,2-dioxaborolan-2-yl)-9,9-bis[3-ethoxycarbonyl-4-[2-[2-(2-methoxyethoxy)ethoxy]ethoxy]phenyl]-fluorene was synthesized by a method described in WO2014/046306.

Compound (1-3): 2,7-dibromo-9,9-bis[3-ethoxycarbonyl-4-[2-[2-(2-methoxyethoxy)ethoxy]ethoxy]phenyl]-fluorene was synthesized by a method described in WO2014/046306.

Example 4

Under a nitrogen atmosphere, 3.66 g of a compound (2-3), 3.30 g of a compound (1-3), 0.06 g of dichlorobis(triphenylphosphine)palladium, 1.20 g of methyltrioctylammonium chloride (manufactured by Sigma-Aldrich, trade name: Aliquat336 (registered trademark)) and 52 g of toluene were mixed, and the mixture was heated at 105° C. Into the resultant mixed liquid, 36 g of a 29% tetraethylammonium hydroxide aqueous solution was dropped, and the mixture was mixed with heating for 0.2 hours at a stirring power of 0.01 kW/m$^3$. The resultant mixture was analyzed by GPC, and the polystyrene-equivalent number-average molecular weight and weight-average molecular weight of the compound (3g-1) were determined. The results are shown in Table 3.

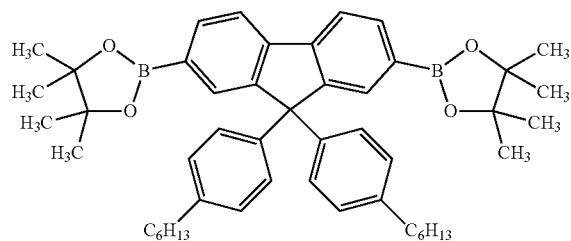

Compound (2-4)

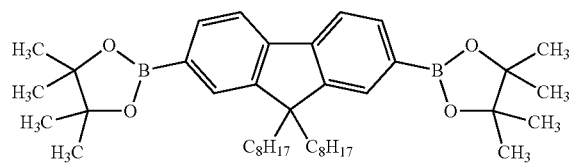

Compound (2-2)

TABLE 3

| | organic base (P) | inorganic base | phase transfer catalyst | number-average molecular weight | weight-average molecular weight |
|---|---|---|---|---|---|
| Comparative Example 3 | none | 2M sodium carbonate aqueous solution | methyltrioctyl ammonium chloride | 1000 | 3000 |
| Example 4 | 29% tetraethylammonium hydroxide aqueous solution | none | methyltrioctyl ammonium chloride | 19000 | 116000 |

The number-average molecular weight and the weight-average molecular weight of the compound (3g-1) obtained after the reaction of 0.2 hours in Example 4 were higher than the number-average molecular weight and the weight-average molecular weight of the compound (3g-1) obtained after the reaction of 0.2 hours in Comparative Example 3, teaching that the production method for the present invention gives a higher reaction rate.

Comparative Example 4

Under a nitrogen atmosphere, 4.79 g of a compound (2-4), 1.62 g of a compound (2-2), 4.97 g of a compound (1-4), 0.80 g of a compound (1-5), 0.01 g of a compound (1-6), 0.09 g of a compound (1-7), 0.03 g of a compound (1-8), 0.03 g of tetrakis(triphenylphosphine)palladium and 78 g of toluene were mixed. To the mixture was added 30 g of a 20% tetraethylammonium hydroxide aqueous solution, and the mixture was mixed with heating for 3 hours at a stirring power of 0.01 kW/m$^3$. The resultant mixture was analyzed by GPC, and the polystyrene-equivalent number-average molecular weight and weight-average molecular weight of the polymer compound were determined. The results are shown in Table 4.

-continued

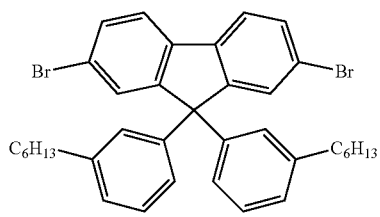

Compound (1-4)

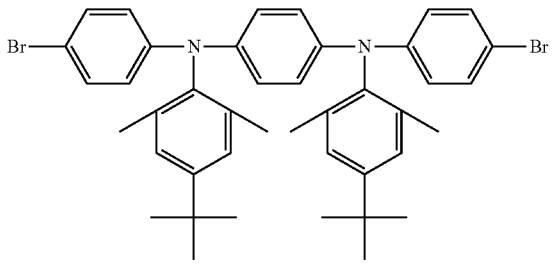

Compound (1-5)

Compound (1-6)

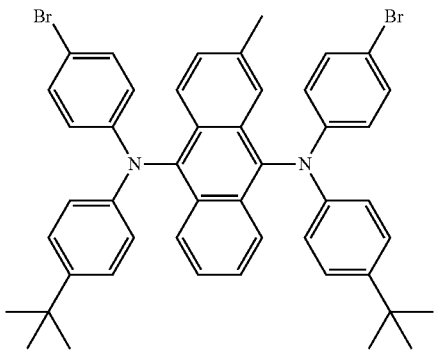

Compound (1-7)

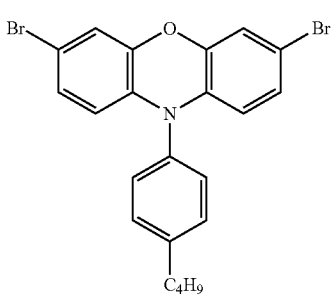

Compound (1-8)

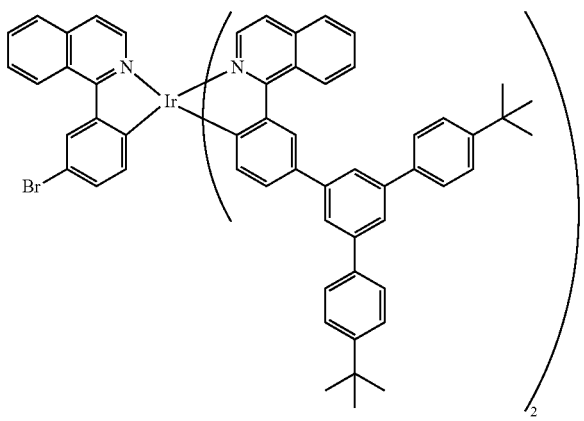

Compound (2-4): 2,7-bis(4,4,5,5-tetramethyl-1,3,2-dioxaborolan-2-yl)-9,9-bis[4-(hexyl)phenyl]-fluorene was synthesized by a method described in WO2012/086671.

Compound (2-2): 2,7-bis(4,4,5,5-tetramethyl-1,3,2-dioxaborolan-2-yl)-9,9-dioctylfluorene was synthesized by a method described in U.S. Pat. No. 6,169,163.

Compound (1-4): 2,7-dibromo-9,9-bis(3-phenyl)fluorene was synthesized by a method described in WO2011/078391.

Compound (1-5): N,N'-bis(4-bromophenyl)-N,N'-bis(4-butyl-2,6-dimethylphenyl)-1,4-phenylenediamine was synthesized by a method described in WO2005/056633.

Compound (1-6): N,N'-bis(4-bromophenyl)-N,N'-bis(4-methylphenyl)-9,10-anthracenediamine was synthesized by a method described in WO2008/143272.

Compound (1-7): 3,7-dibromo-N-(4-butylphenyl)phenoxazine was synthesized by a method described in US patent No. 2004/0127666.

Compound (1-8): It was synthesized by a method described in WO2012/052713.

Example 5

Under a nitrogen atmosphere, 4.79 g of a compound (2-4), 1.62 g of a compound (2-5), 4.97 g of a compound (1-4), 0.80 g of a compound (1-5), 0.01 g of a compound (1-6), 0.09 g of a compound (1-7), 0.03 g of a compound (1-8), 0.03 g of tetrakis(triphenylphosphine)palladium, 0.01 g of tetrabutylammonium bromide and 78 g of toluene were mixed. To the mixture was added 30 g of a 20% tetraethylammonium hydroxide aqueous solution, and the mixture was mixed with heating for 3 hours at a stirring power of 0.01 kW/m$^3$. The resultant mixture was analyzed by GPC, and the polystyrene-equivalent number-average molecular weight and weight-average molecular weight of the polymer compound were determined. The results are shown in Table 4.

TABLE 4

|  | organic base (P) | phase transfer catalyst | number-average molecular weight | weight-average molecular weight |
|---|---|---|---|---|
| Comparative Example 4 | 20% tetraethylammonium hydroxide aqueous solution | none | 14000 | 56000 |
| Example 5 | 20% tetraethylammonium hydroxide aqueous solution | tetrabutylammonium bromide | 49000 | 249000 |

The number-average molecular weight and the weight-average molecular weight of the polymer compound obtained after the reaction of 3 hours in Example 5 were higher than the number-average molecular weight and the weight-average molecular weight of the polymer compound obtained after the reaction of 3 hours in Comparative Example 4, teaching that the production method for the present invention gives a higher reaction rate.

INDUSTRIAL APPLICABILITY

The present invention is useful as a method for producing a compound which manifests a high reaction rate.

The invention claimed is:

1. A method for producing a compound, the method comprising mixing a first compound having two leaving groups, a second compound having two boron atom-containing leaving groups, an organic base, and a phase transfer catalyst having a larger number of carbon atoms than the organic base in the presence of a divalent palladium catalyst, such that the method performs a coupling reaction between the first compound and the second compound.

2. The method for producing a compound according to claim 1, wherein the leaving groups of the first compound are selected from halogen atoms, diazonio groups or groups represented by —O—S(=O)$_2$R$^{C1}$, wherein R$^{C1}$ represents optionally substituted alkyl or aryl groups.

3. The method for producing a compound according to claim 1, wherein the phase transfer catalyst is an ammonium compound.

4. The method for producing a compound according to claim 3, wherein the ammonium compound has 16 to 60 carbon atoms.

5. The method for producing a compound according to claim 1, wherein the phase transfer catalyst is at least one selected from the group consisting of (C$_4$H$_9$)$_4$NF, (C$_4$H$_9$)$_4$NCl, (C$_4$H$_9$)$_4$NBr, (C$_4$H$_9$)$_4$NI, (C$_5$H$_{11}$)$_4$NCl, (C$_5$H$_{11}$)$_4$NBr, (C$_5$H$_{11}$)$_4$NI, (C$_{16}$H$_{33}$)(CH$_3$)$_3$NCl, (C$_8$H$_{17}$)$_3$(CH$_3$)NCl, (C$_8$H$_{17}$)$_2$(C$_{10}$H$_{21}$)(CH$_3$)NCl, (C$_8$H$_{17}$)(C$_{10}$H$_2$O$_2$(CH$_3$)NCl, (C$_{10}$H$_{21}$)$_3$(CH$_3$)NCl, and (C$_8$H$_{17}$)$_4$NBr.

6. The method for producing a compound according to claim 1, wherein the organic base is an organic base having 4 to 15 carbon atoms.

7. The method for producing a compound according to claim 1, wherein the organic base is an ammonium hydroxide compound having 4 to 15 carbon atoms.

8. A method for producing a compound, the method comprising mixing a first compound having two leaving groups, a second compound having two boron atom-containing leaving groups, a first organic base, and a second organic base larger in number of carbon atoms than the first organic base in the presence of a divalent palladium catalyst, such that the method performs a coupling reaction between the first compound and the second compound, and wherein the second organic base is an ammonium hydroxide compound having 16 to 60 carbon atoms.

9. The method for producing a compound according to claim 1, wherein the first compound is a compound represented by the formula (A) and the second compound is a compound represented by the formula (B):

(A)

(B)

wherein R$^1$ and R$^2$ each independently represent an organic group,

X$^1$ represents Cl, Br, I or —O—S(=O)$_2$R$^{C1}$, wherein R$^{C1}$ represents an alkyl group or an aryl group and these groups optionally have a substituent, X$^2$ represents B(R$^{C2}$)$_2$, B(ORC$^{C2}$)$_2$ or BF$_3$T, wherein R$^{C2}$ represents a hydrogen atom, an alkyl group or an aryl group and these groups optionally have a substituent, and the R$^{C2}$ s may be the same or different and they may be combined together to form a ring together with the boron atom to which they are attached or together with the oxygen atoms to which they are attached and the boron atom to which the oxygen atoms are attached, and T represents Li, Na, K, Rb or Cs, and n and m each represent 2.

10. The method for producing a compound according to claim 9, wherein R$^1$ and R$^2$ each independently represent an organic group having 1 to 60 carbon atoms.

11. The method for producing a compound according to claim 10, wherein the organic group is an aromatic group having 6 to 20 carbon atoms and optionally having a substituent.

12. The method for producing a compound according to claim 1, wherein the divalent palladium catalyst is dichlorobis(triphenylphosphine)palladium, dichlorobis[tris(2-methoxyphenyl)phosphine]palladium, dichlorobis[dicyclopentyl(2-methoxyphenyl)phosphine]palladium, dichlorobis[dicyclopentyl(2,6-dimethoxyphenyl)phosphine]palladium or bis[di-tert-butyl(3,5-di-tert-butylphenyl)phosphine]dichloropalladium.

* * * * *